United States Patent [19]
Budge et al.

[11] Patent Number: 5,969,164
[45] Date of Patent: Oct. 19, 1999

[54] CATALYSTS FOR THE HYDROGENATION OF MALEIC ACID TO 1,4-BUTANEDIOL

[75] Inventors: John Raymond Budge, Beachwood; Thomas George Attig, Aurora; Robert Allen Dubbert, Solon, all of Ohio

[73] Assignee: The Standard Oil Company, Chicago, Ill.

[21] Appl. No.: 09/056,193

[22] Filed: Apr. 6, 1998

Related U.S. Application Data

[63] Continuation-in-part of application No. 08/781,945, Dec. 20, 1996, abandoned.

[51] Int. Cl.⁶ .................................................. C07D 307/02
[52] U.S. Cl. ........................... 549/508; 502/113; 568/885
[58] Field of Search ............................. 549/508; 502/113; 568/885

[56] References Cited

U.S. PATENT DOCUMENTS 4,985,572  1/1991  Kitson et al. ............................ 549/326

*Primary Examiner*—Amelia Owens
*Attorney, Agent, or Firm*—David P. Yusko; Stephen L. Hensley

[57] ABSTRACT

An improved catalyst for the hydrogenation of maleic acid, maleic anhydride or other hydrogenatable precursor to 1,4-butanediol and tetrahydrofuran has been discovered. This hydrogenation catalyst comprises palladium, silver, rhenium and at least one of iron, aluminum, cobalt and mixtures thereof, all on a carbon support.

25 Claims, No Drawings

CATALYSTS FOR THE HYDROGENATION OF MALEIC ACID TO 1,4-BUTANEDIOL

REFERENCE TO RELATED APPLICATIONS

This is a continuation-in-part of application Ser. No. 08/781,945 filed on Dec. 20, 1996, now abandoned.

BACKGROUND OF THE INVENTION

1. Field of the Invention

This invention relates to an improved catalyst for the hydrogenation of maleic acid, maleic anhydride or other hydrogenatable precursor to 1,4-butanediol and tetrahydrofuran. The catalyst comprises palladium, silver, rhenium and at least one of iron, aluminum, cobalt and mixtures thereof, all on a carbon support. The use of this catalyst in processes for the hydrogenation of maleic acid, maleic anhydride or other hydrogenatable precursor to 1,4-butanediol and tetrahydrofuran is characterized by higher overall activity to reaction products and by higher yields of 1,4-butanediol with minimal formation of gamma-butyrolactone by-products.

2. Description of the Prior Art

It is well known that tetrahydrofuran, gamma-butyrolactone and 1,4-butanediol are obtained by the catalytic hydrogenation of maleic anhydride and related compounds. Tetrahydrofuran is a useful solvent for natural and synthetic resins and is a valuable intermediate in the manufacture of a number of chemicals and plastics. Gamma-butyrolactone is an intermediate for the synthesis of butyric acid compounds, polyvinylpyrrolidone and methionine. Gamma-butyrolactone is a useful solvent for acrylate and styrene polymers and also a useful ingredient of paint removers and textile assistants. 1,4-butanediol (a.k.a. 1,4-butylene glycol) is useful as a solvent, a humectant, an intermediate for plasticizers and pharmaceuticals, a cross-linking agent for polyurethane elastomers, a precursor in the manufacture of tetrahydrofuran, and is used to make terephthalate plastics.

Of particular interest in the instant invention are hydrogenation catalysts comprising palladium, silver, rhenium and at least one of iron, aluminum, cobalt and mixtures thereof, all on a carbon support, which are useful for the hydrogenation of maleic anhydride, maleic acid and related compounds to tetrahydrofuran, gamma-butyrolactone and 1,4-butanediol.

British Patent No. 1,534,232 teaches the hydrogenation of carboxylic acids, lactones or anhydrides using a hydrogenation catalyst consisting of palladium and rhenium on a carbon support. U.S. Pat. Nos. 4,550,185 and 4,609,636 teach a process of making tetrahydrofuran and 1,4-butanediol by hydrogenating maleic acid, maleic anhydride or other hydrogenatable precursor in the presence of a catalyst comprising palladium and rhenium on a carbon support wherein the palladium and rhenium were present in the form of crystallites having an average palladium crystallite size of about 10 to 25 nm and an average rhenium crystallite size of less than 2.5 nm. The preparation of this catalyst is characterized by the deposition and reduction of the palladium species on the carbon support followed by the deposition and reduction of the rhenium species on the palladium impregnated carbon support.

U.S. Pat. No. 4,985,572 teaches a process for the catalytic hydrogenation of a carboxylic acid or an anhydride thereof to the corresponding alcohol and/or carboxylic acid ester using a catalyst comprising rhenium, palladium and at least one other metal capable of alloying with the palladium, all on a carbon support. The preferred metal capable of alloying with the palladium is silver but gold, copper, nickel, rhodium, tin, cobalt, aluminum, manganese, gallium, iron, chromium, and platinum also are taught. The preparation of this catalyst is characterized by the simultaneous deposition of palladium and silver on the carbon support followed by a high temperature (600° C.) heat treatment. Rhenium is then deposited on the palladium/alloying metal impregnated carbon support. The resulting catalyst is then reduced.

WO 92/02298 discloses a hydrogenation catalyst comprising palladium and rhenium and one or more metals selected from the group consisting of rhodium, cobalt, platinum, ruthenium, iron, thulium, cerium, yttrium, neodymium, aluminum, praseodymium, holmium, hafnium, manganese, vanadium, chromium, gold, terbium, lutetium, nickel, scandium and niobium, on a support.

Generally, in the hydrogenation of maleic acid, maleic anhydride or other hydrogenatable precursor the above discussed catalysts have the propensity to produce more tetrahydrofuran and gamma-butyrolactone than 1,4-butanediol. An object of this invention is a process and a catalyst which will maximize 1,4-butanediol production and minimize gamma-butyrolactone production.

SUMMARY OF THE INVENTION

The instant invention is a catalyst comprising palladium, silver, rhenium and at least one of iron, aluminum, cobalt and mixtures thereof, all on a carbon support and the use of this catalyst in a process for the production of 1,4-butanediol comprising catalytically hydrogenating a hydrogenatable precursor in contact with a hydrogen-containing gas.

Another embodiment of the instant invention is a method for making such catalyst for the production of 1,4-butanediol comprising:

(i) oxidizing a carbon support by contacting the carbon support with an oxidizing agent;

(ii) impregnating in one or more impregnation steps comprising contacting a carbon support with a source of palladium, silver, rhenium and at least one of iron, aluminum, cobalt and mixtures thereof;

(iii) drying the impregnated carbon support to remove solvent after each impregnation step; and (iv) heating the impregnated carbon support from ambient temperature to a temperature of between about 100° C. and about 350° C. under reducing conditions.

DETAILED DESCRIPTION OF THE INVENTION

A catalyst comprising palladium, rhenium, silver and at least one of iron, aluminum, cobalt and mixtures thereof, all on a carbon support is employed in the hydrogenation of a hydrogenatable precursor to provide high yields of 1,4-butanediol and smaller yields of tetrahydrofuran with minimal gamma-butyrolactone formation.

The Reactants

In the process of the instant invention, at least one hydrogenatable precursor is reacted with a hydrogen containing gas in the presence of the catalyst. As used herein a "hydrogenatable precursor" is any carboxylic acid or anhydride thereof, carboxylic acid ester, lactone or mixture thereof which when hydrogenated produces 1,4-butanediol. Representative hydrogenatable precursors include maleic acid, maleic anhydride, fumaric acid, succinic anhydride, succinic acid, succinate esters such as dimethyl succinate, maleate esters such as dimethyl maleate, gamma-butyrolactone or mixtures thereof. The preferred hydrogenatable precursors are maleic acid, maleic anhydride, succinic acid, succinic anhydride or mixtures thereof.

The most preferred hydrogenatable precursor is maleic acid which is typically obtained by reacting n-butane or benzene in an oxygen-containing gas in the presence of a catalyst to oxidize in the vapor phase the n-butane or benzene to maleic anhydride, and then collecting the maleic anhydride by a water quench to produce maleic acid in an aqueous solution. The oxidation of n-butane or benzene is typically operated at a temperature of about 300° C. to 600° C. and a pressure of about 0.5 to 20 atmospheres (50 to 2000 kPa).

Typically, the hydrogen ($H_2$) containing gas is commercially pure hydrogen with no diluent gases. However, the hydrogen containing gas in addition to hydrogen ($H_2$) may also contain nitrogen (N2), any gaseous hydrocarbon (e.g. methane), as well as gaseous oxides of carbon, (e.g. carbon monoxide, carbon dioxide).

The Catalyst

The catalyst employed in the instant invention comprises palladium, silver, rhenium and at least one of iron, aluminum, cobalt and mixtures thereof, all supported on carbon. The carbons for use in this invention have a BET surface area of at least 200 $m^2/g$, and preferably be in the range of 500–1500 $m^2/g$.

The catalyst composition comprises about 0.1 to about 20 weight percent palladium, preferably about 2 to about 8 weight percent palladium, more preferably about 2 to about 4 weight percent palladium; about 0.1 to about 20 weight percent silver, preferably about 1 to about 8 weight percent silver, more preferably about 2 to about 4 weight percent silver; about 0.1 to about 20 weight percent rhenium, preferably about 1 to about 10 weight percent rhenium, more preferably about 5 to about 9 weight percent rhenium; and about 0.01 to about 10 weight percent of at least one of iron, aluminum, cobalt and mixtures thereof, preferably about 0.1 g to about 5 weight percent of at least one of iron, aluminum, cobalt and mixtures thereof, more preferably about 0.2 to about 0.6 weight percent of at least one of iron, aluminum, cobalt and mixtures thereof. The ratio of palladium to silver is between 10 to 1 and to 10. The catalyst composition may also be further modified through the incorporation of a metal or metals selected from Groups IA, IIA or VIII.

The catalysts of this invention may be conveniently prepared by oxidizing the carbon support (however this treatment step is optional) followed by impregnation of the carbon support, either in single or multiple impregnation steps, with a solution or solutions containing at least one palladium, silver, rhenium or at iron, aluminum, cobalt compound.

Preferably, the carbon support is first oxidized by contacting the carbon support, prior to deposition of the metals, with a oxidizing agent. Catalysts prepared in this manner show a dramatic improvement in activity and selectivity over catalysts prepared with non-oxidized carbon support. A number of oxidizing agents such as nitric acid, hydrogen peroxide, sodium hypochlorite, ammonium persulfate, perchloric acid, and oxygen may be effective in this process. Liquid phase oxidizing agents are preferred. Nitric acid at elevated temperatures has been found to be especially effective for this procedure. Gaseous phase oxidizing agents include any oxygen-containing gas, e.g. air. Gaseous oxidizing agents are contacted with the carbon support at temperatures of about 200° C. or greater and at pressures of about atmospheric or greater. Optionally one or more metals, such as iron, nickel, palladium, rhenium, silver, gold copper, rhodium, tin, cobalt, manganese, gallium, and platinum, may be admixed with the oxidizing agent and subsequently deposited on the carbon support during the oxidizing agent pretreatment of the carbon support.

As stated earlier, the catalysts of this invention are prepared by impregnation of the carbon support, either in single or multiple impregnation steps, with a solution or solutions containing at least one palladium, silver, rhenium, iron, aluminum or cobalt compound. As used herein, impregnation of the carbon support means to cause the carbon support to be filled, imbued, permeated, saturated or coated. The impregnating solution may optionally contain complexing agents to help solubilize one or more of the metal compounds. The impregnating solution may also optionally be combined with the oxidizing agent prior to or in situ with contacting the carbon support. The catalyst is dried after each impregnation step to remove any carrier solvent. Drying temperatures are between about 80° C. and about 150° C.

The solutions of palladium compound, silver compound, rhenium compound, iron compound, aluminum compound, cobalt compound or mixtures thereof can be applied to the carbon by immersing or suspending the support material in the solution or by spraying the solution onto the carbon. The solution containing the palladium compound is typically an aqueous solution containing an amount of palladium compound to yield a catalyst product with the requisite amount of palladium. The palladium compound may be palladium nitrate or a palladium compound such as a chloride, carbonate, carboxylate, acetate, acetyl acetonate, or amine. The solution containing the silver compound is typically an aqueous one containing an amount of silver compound to yield a catalyst product with the requisite amount of silver. The palladium and silver compounds should be thermally decomposable and reducible to the metals. The solution containing the rhenium compound is typically an aqueous one containing an amount of rhenium compound to yield a catalyst product with the requisite amount of rhenium. The rhenium compound is typically perrhenic acid, ammonium perrhenate or an alkali metal perrhenate. The solution containing the iron compound is typically an aqueous one containing an amount of iron compound to yield a catalyst product with the requisite amount of iron. The iron compound is typically ferric nitrate, but other suitable iron containing compounds include, but are not limited to, ferrous acetate, ferric acetate, ferrous chloride, ferrous fumarate, and ferric fumarate. The solution containing the aluminum compound is typically an aqueous one containing an amount of aluminum compound to yield a catalyst product with the requisite amount of aluminum. The aluminum compound is typically aluminum nitrate, but other suitable aluminum containing compounds include, but are not limited to, aluminum acetate, aluminum acetate and aluminum chloride. The solution containing the cobalt compound is typically an aqueous one containing an amount of cobalt compound to yield a catalyst product with the requisite amount of cobalt. The cobalt compound is typically cobalt nitrate, but other suitable cobalt containing compounds include, but are not limited to, cobalt acetate, cobalt chloride, cobalt maleate, and cobalt fumarate.

The impregnating solution(s) may optionally contain metal complexing agents to help solubilize one or more of the metal compounds. The addition of acetonitrile to the impregnating solution allows the Pd, Ag, and Re compounds be added in a single step. Nitric acid or other oxidizing agent may also be added to the impregnating solution.

After impregnation with palladium, silver, rhenium and at least one of iron, aluminum, cobalt and mixtures thereof and then drying the impregnated carbon support, the catalyst is activated by heating the impregnated carbon support under reducing conditions from ambient temperature (i.e. typically room temperature) to a temperature of between about 120° C. and 350° C., preferably between about 150° C. and about 300° C. Hydrogen, or a mixture of hydrogen and nitrogen, in contact with the catalyst may be conveniently used for the catalyst reduction. Reduction of the impregnated carbon support is only after the carbon support has been impregnated with palladium, silver, rhenium and at least one of iron, aluminum, cobalt and mixtures thereof. In the case of multiple impregnation steps and multiple dryings, the reduction of the catalyst is done after the final drying.

The palladium in catalysts of the present invention is present in the form of crystallites having an average crystallite size of less than 100 angstroms (10 nm). More specifically, when freshly reduced samples of the palladium/ silver/rhenium on a carbon support as used herein are analyzed by X-ray diffraction (XRD) and Scanning Transmission Electron Microscopy (STEM), the palladium containing particles (i.e. particles of palladium, particles of palladium and silver, or particles of palladium and rhenium) in the catalyst are finely dispersed and have a mean crystallite size of less than about 50 angstroms (5 nm). As used herein the "particle size distribution" and "mean particle size" are as defined in "Structure of Metal Catalysts" by J. R. Anderson, pages 358–359, Academic Press (1975), which is incorporated herein by reference.

Lastly the preparation of the catalysts described herein does not employ large amounts of excess water which must be removed during the drying step nor does it employ a high temperature (i.e. about 600° C.) treatment step as taught in U.S. Pat. No. 4,985,572.

Upon completion of the catalyst preparation described herein, iron, aluminum, or cobalt are present in the catalyst. However, during the hydrogenation of maleic acid and depending upon the conditions in the hydrogenation reactor, some iron, aluminum or cobalt may be leached from the catalyst. In the case of PdAgReFe on carbon catalysts, the leaching of iron from the catalyst has on occasion been observed to be extensive, such that no iron was detected in the catalyst after several weeks on stream.

The Process

The method for carrying out the process comprises reacting a hydrogenatable precursor with a hydrogen-containing gas in the presence of the hydrogenation catalyst, and recovering and purifying the reaction products by distillation.

The liquid phase hydrogenation of this invention can be run using conventional apparatus and techniques in a stirred-tank reactor or in a fixed-bed reactor. Single or multiple-stage reactors may be employed. The amount of catalyst required will vary widely and is dependent upon a number of factors such as reactor size and design, contact time and the like.

The hydrogen-containing gas is fed continuously, generally with the hydrogen in considerable stoichiometric excess to the other reactants. Unreacted hydrogen can be returned to the reactor as a recycle stream. The precursor solution, e.g., maleic acid solution, is fed continuously at concentrations ranging from dilute solutions to near the maximum solubility level, typically about 30 to about 50 weight percent.

Preferably the hydrogenation step is run at a temperature of about 50° C. to 350° C., and a hydrogen pressure of about 20–400 atmospheres with hydrogen to hydrogenatable precursor ratios ($H_2/P$) of between 5 to 1 and 1000 to 1 and contact times of 0.1 minute to 20 hours. For maximum 1,4-butanediol production the reaction temperature is between about 50° C. and 250° C. and more preferably between about 80° C. and 200° C.

The reaction products, 1,4-butanediol, tetrahydrofuran, gamma-butyrolactone or mixtures thereof, are advantageously separated by fractional distillation. By-products which are formed in small amounts or unreacted feed, such as for example, succinic anhydride or succinic acid, are optionally returned to the hydrogenation stage. The gamma-butyrolactone may also be recycled to the hydrogenation reactor.

Using the process of this invention, more specifically using the hydrogenation catalyst described herein, maleic acid is converted virtually quantitatively in a simple reaction. The yields of 1,4-butanediol and tetrahydrofuran achieved are about 80 mole percent or greater, typically about 90 mole percent or greater, with a majority portion of the yield being 1,4-butanediol. Reaction by-products may include n-butanol, n-butyric acid, n-propanol, propionic acid, methane, propane, n-butane, carbon monoxide, and carbon dioxide. However, the formation of non-utilizable by-products is slight.

SPECIFIC EMBODIMENTS

In order to illustrate the instant invention the following examples are provided.

COMPARATIVE EXAMPLE A

Preparation of PdAgRe on carbon 45 g of concentrated nitric acid (70 wt %) was diluted to 50 cc with deionized water. This solution was used to impregnate 74.6 g of CECA 1.5 mm ACL40 carbon extrudate. During the impregnation the flask was occasionally cooled. The mixture was allowed to stand for 80 minutes, and then dried at 130° C. for 3 h. This procedure was repeated with a 35 minute standing time and a 16 h drying time.

35.1 g of palladium nitrate solution (8.5 wt % Pd), 11.95 g of perrhenic acid (53.3 wt % Re) solution and 7.9 g of concentrated (70 wt % nitric acid), were diluted to 50 cc with deionized water. The ACL40 was then gradually impregnated with the Pd+Re solution. The flask was occasionally cooled during the impregnation. The mixture was allowed to stand for 2 h, and then dried at 130° C. for 2 h.

4.7 g of silver nitrate and 7.9 g of concentrated nitric acid were diluted to 50 cc with deionized water. The PdRe/ ACL40 was then gradually impregnated with the silver nitrate solution with occasional cooling of the flask. The mixture was allowed to stand for 3.5 h, and then dried at 130° C. for 64 h. The resulting catalyst was 3.3 wt % Pd/3.3 wt % Ag/7.1 wt % Re.

EXAMPLE 1

Preparation of PdAgReFe on carbon 45 g of concentrated nitric acid (70 wt %) and 1 g of ferric nitrate ($Fe(NO_3)_3 9H_2O$) were diluted to 50 cc with deionized water. This solution was used to impregnate 74.6 g of CECA 1.5 mm ACL40 carbon extrudate. During the impregnation the flask was occasionally cooled. The mixture was allowed to stand for 65 minutes, and then dried at 130° C. for 2 h. This procedure was repeated with a 65 minute standing time and a 2.4 h drying time.

35.1 of palladium nitrate solution (8.5 wt % Pd), 11.95 g of perrhenic acid (53.3 wt % Re) solution, 7.9 g of concentrated nitric acid (70 wt %), were diluted to 50 cc with deionized water. The ACL40 was then gradually impregnated with the Pd/Re solution. The flask was occasionally cooled during the impregnation. The mixture was allowed to stand for 2.5 h, and then dried at 130° C. for 2.25 h.

4.7 g of silver nitrate and 7.9 g of concentrated nitric acid were diluted to 50 cc with deionized water. The PdRe/ACL40 was then gradually impregnated with the silver nitrate solution with occasional cooling of the flask. The mixture was allowed to stand for 80 minutes, and then dried at 130° C. for 69 h. The resulting catalyst was 3.3 wt % Pd/3.3 wt % Ag/7.1 wt % Re/0.3 wt % Fe.

EXAMPLE 2

Hydrogenation of Aqueous Maleic Acid and Catalyst Testing

The catalyst of Comparative Example A and Example 1 were each tested in two Hastelloy C276 reactors connected in series using heated Hastelloy C276 tubing. The reactors had an internal diameter of 0.516", and each was fitted with a ⅛" axial Hastelloy C276 thermowell.

Each catalyst was mixed with 50/70 mesh quartz chips (0.625 g quartz per g of catalyst) before charging to the reactor. 20 cc (12.15 g) of catalyst was placed in the first reactor, and 40 cc (24.3 g) in the second reactor. Prior to testing the catalyst was reduced at atmospheric pressure in flowing hydrogen (400 sccm) with the following temperature ramp:

Room Temperature to 30° C. over 5 hours
30° C. to 100° C. over 2 hours
100° C to 230° C. over 11 hours
maintain 230° C. for 5 hours The reactors were operated with hydrogen recycle. A small portion of the hydrogen was vented to prevent the accumulation of non-condensable gases. The maleic acid concentration in the liquid feed was 35.5 wt %. The process conditions for the catalyst testing were as following process conditions:

Pressure: 2500 psig
$H_2$/Maleic Acid Feed Ratio: 88
$H_2$ Make-up to Recycle Ratio: 0.083
First Reactor: Average Set Temperature: 100° C. LHSV; 1.6 $h^{-1}$
Second Reactor:
Average Set Temperature: 153–162° C.
LHSV: 0.8 $h^{-1}$ Table 1 summarizes the results of the testing on the PdAgRe/C and PdAgReFe/C catalysts. Product selectivity's were calculated on a molar $C_4$ basis.

TABLE 1

Catalyst Performance Data

| Catalyst | Hrs. on Stream | Temp. (C) | % BDO sel | % THF sel | % GBL sel | % BuOH sel | % SAC sel |
|---|---|---|---|---|---|---|---|
| PdAgReFe/C (Ex. 1) | 185 | 153 | 89.5 | 5.6 | 0.6 | 4.0 | 0.05 |
| PdAgRe/C (Comp. Ex) | 185 | 162 | 86.3 | 8.8 | 0.9 | 3.8 | 0.08 |

Table 1 illustrates that the BDO yield is significantly higher for PdAgReFe/C. Table 1 also illustrates that the iron containing catalyst (Example 1) is more active than the non iron containing species (Comparative Example). This is evidenced by better overall conversions at the lower reaction temperature.

EXAMPLE 3

Preparation of PdAgReM on Carbon, where M is Fe, Al, or Co a) Preparation of Precursor PdRe/Norit RX1.5 Extra 584 g of Norit RX1.5 Extra carbon extrudate (acquired from Norit Americas Inc. located in Atlanta, Ga.) was impregnated with 719 g of concentrated nitric acid (70 wt %). The material was allowed to stand for 90 minutes, and was then dried in an oven at 130° C. overnight.

218.1 g of palladium nitrate solution (8.5 wt % Pd in 10 wt % $HNO_3$), 114 g of perrhenic acid (56.36 wt % Re), 234.6 g of concentrated nitric acid, and 151 g of de-ionized water were mixed together. The carbon was impregnated with 96% of the Pd/Re solution, and the mixture allowed to stand for 2 h. After drying overnight at 130° C., 671.7 g of material was obtained, with a Pd content of 2.6 wt %, and Re content of 9.2 wt %. The moisture content (% wt loss at 150° C.) was 3.4 wt %. The material was riffled into eight ~84 g portions.

b) Preparation of PdAgReM/Norit RX1.5 Extra

Three catalysts were made as described below, with M=Fe, Al or Co. The Table below summarizes the materials used for the different catalyst preparations:

TABLE 2

| PdRe/C Riffle Lot #: Wt (g) | Wt. $AgNO_3$ (g) | Wt. $HNO_3$ (70 wt %) | Wt. $H_2O$ (g) | Metal Nitrate M Form | | Weight of Metal Nitrate (g) |
|---|---|---|---|---|---|---|
| 63.4 g | 2.5 | 6.9 | 38 | Fe | $Fe(NO_3)_3 \cdot 9H_2O$ | 2 |
| 63.4 g | 2.5 | 6.9 | 38 | Al | $Al(NO_3)_3 \cdot 9H_2O$ | 1.86 |
| 63.4 g | 2.5 | 6.9 | 38 | Co | $Co(NO_3)_2 \cdot 6H_2O$ | 1.44 |

The preparation for M=Fe is as follows: 2.5 g of silver nitrate, 6.9 g of concentrated nitric acid, and 2 g of $Fe(NO_3)_3 \cdot 9H_2O$, were added to 38 g of deionized water, and the mixture stirred to dissolve the solids. 63.4 g (140 cc) of PdRe/Norit (Riffle Lot 1) was then impregnated with the Ag/Fe solution, and the mixture allowed to stand for about 2.5 h. The material was then place in an oven at 130° C., and dried for 4.5 h. The other catalysts (M=Al or Co) were prepared in a similar manner.

EXAMPLE 4

Hydrogenation of Aqueous Maleic Acid PdAgReM on Carbon Catalyst, where M is Fe, Al, or Co Catalyst testing was carried out using two Hasteloy C276 reactors connected in series using heated Hasteloy C276 tubing. The reactors had an internal diameter of 0.516", and each was fitted with a ⅛" axial Hasteloy C276 thermowell.

The catalyst was mixed with 50/70 mesh quartz chips (0.625 g quartz per g of catalyst) before charging to the reactor. 20 cc (12.15 g) of catalyst was placed in the first reactor, and 40 cc (24.3 g) in the second reactor. Prior to testing the catalyst was reduced at atmospheric pressure in flowing hydrogen (400 sccm) with the following temperature ramp:

RT to 30° C. in 5 h
30–100° C. in 2 h
100–230° C. in 1 h
@230° C. for 5 h

The reactors were operated with hydrogen recycle. A small portion of the hydrogen was vented to prevent the accumulation of non-condensable gases. The maleic acid concentration in the aqueous liquid feed was 35.5 wt %. The process conditions for the catalyst testing were as follows:

Pressure: 2500 psig
$H_2$/(MAC+FAC) Feed Ratio: 88
$H_2$ Make-up to Recycle Ratio: 0.083
First Reactor: Average Set Temperature: 110° C.
LHSV: 1.6 $h^{-1}$
Second Reactor: Average Set Temperature: 153–162° C.
LHSV: 0.8 $h^{-1}$ Table 3 summarizes the results of the testing for the PdAgReM/Norit RX1.5 Extra catalysts.

concentrations, contact times, solids loadings, feedstocks, reaction conditions, and products, if any, can be determined from the total specification disclosure provided, without departing from the spirit of the invention herein disclosed and described, the scope of the invention including modifications and variations that fall within the scope of the attached claims.

The invention claimed is:

1. A catalyst consisting essentially of palladium, silver, rhenium and at least one of iron, aluminum, cobalt and mixtures thereof on a carbon support.

2. The catalyst of claim 1, wherein the catalyst comprises between about 0.1 to about 20 wt % palladium, between about 0.1 to about 20 wt % silver, between about 0.1 to about 20 wt % rhenium, and between about 0.1 to about 5 wt % of at least one of iron, aluminum, cobalt and mixtures thereof.

3. The catalyst of claim 2, wherein the catalyst comprises about 2 to 4 wt % palladium, about 2 to 4 wt % silver, about 5 to 9 wt % rhenium, and about 0.2 to 0.6 wt % of at least one of iron, aluminum, cobalt and mixtures thereof.

4. A process for the production of 1,4-butanediol comprising catalytically hydrogenating a hydrogenatable precursor in contact with a hydrogen-containing gas and a hydrogenation catalyst comprising palladium, silver, rhenium and at least one of iron, aluminum, cobalt and mixtures thereof, on a carbon support.

5. The process of claim 4 wherein the hydrogenatable precursor is selected from the group consisting of maleic acid, maleic anhydride, fumaric acid, succinic acid, succinic anhydride, maleate esters, succinate esters, gamma-butyrolactone and mixtures thereof.

6. The process of claim 4 wherein the hydrogenatable precursor is at least one of maleic acid, succinic acid, or gamma-butyrolactone.

7. The process of claim 4, wherein the catalyst comprises between about 0.1 to about 20 wt % palladium, between about 0.1 to about 20 wt % silver, between about 0.1 to about 20 wt % rhenium, and between about 0.1 to about 5 wt % of at least one of iron, aluminum, cobalt and mixtures thereof.

TABLE 3

Catalyst Performance Data

| Catalyst | TOS | Set T | Mass Bal | BDO sel | THF sel | GBL sel | BuOH sel | PrOH sel | SAC sel |
|---|---|---|---|---|---|---|---|---|---|
| PdAgReAl/C | 14.3 | 165 | 0.97 | 88.15 | 6.51 | 0.22 | 4.30 | 0.42 | 0.03 |
| | 31.8 | 161 | 1.00 | 89.18 | 6.81 | 0.20 | 3.01 | 0.30 | 0.04 |
| | 44.4 | 152 | 0.99 | 91.01 | 4.97 | 1.43 | 1.80 | 0.17 | 0.28 |
| PdAgReCo/C | 19.1 | 165 | 0.97 | 86.92 | 8.07 | 0.22 | 4.12 | 0.55 | 0.02 |
| | 44.5 | 152 | 0.97 | 88.83 | 6.67 | 1.82 | 1.95 | 0.19 | 0.39 |
| | 68.7 | 152 | 0.99 | 87.78 | 7.34 | 2.12 | 1.96 | 0.19 | 0.46 |
| PdAgReFe/C | 19.0 | 165 | 0.98 | 88.70 | 7.82 | 0.23 | 2.79 | 0.32 | 0.01 |
| | 43.1 | 152 | 0.99 | 87.94 | 6.39 | 3.10 | 1.59 | 0.15 | 0.70 |
| | 64.3 | 155 | 1.00 | 88.62 | 7.78 | 1.15 | 1.93 | 0.19 | 0.21 |

TOS = Time on Stream (hrs.)
Set T = Reactor Set Temperature (° C.)
Mass Bal = Mass Balance
BDO Sel = % Selectivity to 1,4-Butanediol
THF sel = % Selectivity to Tetrahydrofuran
GBL sel = % Selectivity to Gammabutyrolactone
BuOH sel = % Selectivity to Butanol
PrOH sel = % Selectivity to Propanol
SAC sel = % Selectivity to Succinic Acid It is to be understood that the subject invention is not to be limited by the examples set forth herein. These have been provided merely to demonstrate operability, and the selection of catalysts, metal sources, carbon supports, 8. The process of claim 7, wherein the catalyst comprises about 2 to 4 wt % palladium, about 2 to 4 wt % silver, about 5 to 9 wt % rhenium, and about 0.2 to 0.6 wt % of at least one of iron, aluminum, cobalt and mixtures thereof.

9. The process of claim 4, wherein the ratio of hydrogen to hydrogenatable precursor is between about 5 to 1 and about 1000 to 1.

10. The process of claim 4, wherein the hydrogen-containing gas pressure is between about 20 and 400 atmospheres.

11. The process of claim 4, wherein the contact time is between about 0.1 minute and 20 hours.

12. A method for making catalyst for the production of 1,4-butanediol comprising
   (i) oxidizing a carbon support by contacting the carbon support with an oxidizing agent;
   (ii) impregnating in one or more impregnation steps comprising contacting a carbon support with a source of palladium, silver, rhenium and at least one of iron, aluminum, cobalt and mixtures thereof;
   (iii) drying the impregnated carbon support to remove solvent after each impregnation step; and
   (iv) heating the impregnated carbon support from ambient temperature to a temperature of between about 100° C. and about 350° C. under reducing conditions.

13. The method of claim 12 wherein the carbon support is contacted with an oxidizing agent at approximately the same time as the impregnation of the carbon support with the source of the palladium, silver, rhenium and at least one of iron, aluminum, cobalt and mixtures thereof.

14. The method of claim 12, wherein the oxidizing agent is selected from the group consisting of nitric acid, hydrogen peroxide, sodium hypochlorite, ammonium persulfate, perchloric acid, and oxygen.

15. The method of claim 12, wherein after step (iv) the catalyst is contacted with a hydrogenatable precursor and hydrogen and heated from ambient temperature to between about 40° C. and about 250° C.

16. The process of claim 12 wherein the hydrogenatable precursor is selected from the group consisting of maleic acid, maleic anhydride, fumaric acid, succinic acid, succinic anhydride, dimethyl succinate, gamma-butyrolactone and mixtures thereof.

17. A process for the production of tetrahydrofuran and 1,4-butanediol comprising catalytically hydrogenating a hydrogenatable precursor in contact with a hydrogenation catalyst comprising palladium, silver, rhenium and at least one of iron, aluminum, cobalt and mixtures thereof, on a carbon support wherein the catalyst is prepared by the steps of (i) oxidizing a carbon support by contacting the carbon support with an oxidizing agent;
   (ii) impregnating in one or more impregnation steps comprising contacting the carbon support with a source of palladium, silver, rhenium and at least one of iron, aluminum, cobalt and mixtures thereof;
   (iii) drying the impregnated carbon support to remove solvent after each impregnation step; and
   (iv) heating the impregnated carbon support from ambient temperature to a temperature of between about 100° C. and about 350° C. under reducing conditions.

18. The process of claim 17 wherein the hydrogenatable precursor is selected from the group consisting of maleic acid, maleic anhydride, fumaric acid, succinic acid, succinic anhydride, maleate esters, succinate esters, gamma-butyrolactone and mixtures thereof.

19. The process of claim 17 wherein the hydrogenatable precursor is at least one of maleic acid, succinic acid, or gamma-butyrolactone.

20. The process of claim 17, wherein the catalyst comprises between about 0.1 to about 20 wt % palladium, between about 0.1 to about 20 wt % silver, between about 0.1 to about 20 wt % rhenium, and between about 0.1 to about 5 wt % of at least one of iron, aluminum, cobalt and mixtures thereof.

21. The process of claim 17, wherein the catalyst comprises about 2 to 4 wt % palladium, about 2 to 4 wt % silver, about 5 to 9 wt % rhenium, and about 0.2 to 0.6 wt % of at least one of iron, aluminum, cobalt and mixtures thereof.

22. The process of claim 17, wherein the ratio of hydrogen to hydrogenatable precursor is between about 5 to 1 and about 1000 to 1.

23. The process of claim 17, wherein the hydrogen-containing gas pressure is between about 20 and 400 atmospheres.

24. The process of claim 17, wherein the contact time is between about 0.1 minute and 20 hours.

25. The method of claim 17, wherein the oxidizing agent is selected from the group consisting of nitric acid, hydrogen peroxide, sodium hypochlorite, ammonium persulfate, perchloric acid, and oxygen.

* * * * *

UNITED STATES PATENT AND TRADEMARK OFFICE
CERTIFICATE OF CORRECTION

PATENT NO. : 5,969,164
DATED : Oct. 19, 1999
INVENTOR(S) : John Raymond Budge, Thomas George Attig, Robert Allen Dubbert It is certified that error appears in the above-identified patent and that said Letters Patent is hereby corrected as shown below:

| Col. | Line | |
|---|---|---|
| 3 | 41,42 | "0.1 g to about 5" should read: "0.1 to about 5" |
| 6 | 6,7 | "precurs or ratios" should read: "precursor ratios" |
| 6 | 64 | "(Fe(NO$_3$)$_3$ 9H$_2$O)" should read: "(Fe(NO$_3$)$_3$•9H$_2$O)" |
| 9 | 22 | "100-230°C in 1 h" should read: "100-230°C in 11 h" |

Signed and Sealed this

Twelfth Day of September, 2000

Attest:

Q. TODD DICKINSON

*Attesting Officer*  *Director of Patents and Trademarks*